Figure 1:
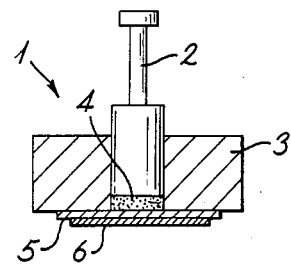

United States Patent [19]
Fray et al.

[11] Patent Number: 4,879,005
[45] Date of Patent: Nov. 7, 1989

[54] ELECTROCHEMICAL SENSOR FOR HYDROGEN SENSING

[75] Inventors: Derek J. Fray, Cambridge, England; David R. Morris, New Brunswick, Canada

[73] Assignee: National Research Development Corporation, London, England

[21] Appl. No.: 247,567

[22] Filed: Sep. 22, 1988

[30] Foreign Application Priority Data

Oct. 2, 1987 [GB] United Kingdom ............... 8723222

[51] Int. Cl.$^4$ ............................................. G01N 27/58
[52] U.S. Cl. .................................. 204/1 T; 204/422; 204/424; 204/426
[58] Field of Search ............... 204/424, 421, 1 T, 422, 204/423, 426; 429/191, 192

[56] References Cited

U.S. PATENT DOCUMENTS

| | | | |
|---|---|---|---|
| 3,410,780 | 11/1968 | Holden | 204/1 T X |
| 3,727,058 | 4/1973 | Schrey | 204/424 X |
| 4,179,491 | 12/1979 | Howe et al. | 204/1 T X |
| 4,293,399 | 10/1981 | Belanger et al. | 204/424 |
| 4,478,704 | 10/1984 | Miyoshi et al. | 204/412 |
| 4,664,757 | 5/1987 | Zupancic et al. | 204/1 T |
| 4,718,991 | 1/1988 | Yamazoe et al. | 204/1 T |

Primary Examiner—G. L. Kaplan
Attorney, Agent, or Firm—Nixon & Vanderhye

[57] ABSTRACT

An electrochemical sensor for hydrogen has, as its reference, a metal having a choice of oxidation states, the metal redox reaction comprising the reference.

The sensor preferably comprises
(i) a platinum-black electrode 6 which is electronically conductive and in which the hydrogen to be sensed is mobile,
(ii) a solid-state conductor 5 for protons, and
(iii) a mixture 4 of $FeSO_4$ and $Fe_2(SO_4)_3$ powders, with the Fe(II)/Fe(III) redox reaction in this mixture providing the hydrogen reference.

13 Claims, 2 Drawing Sheets

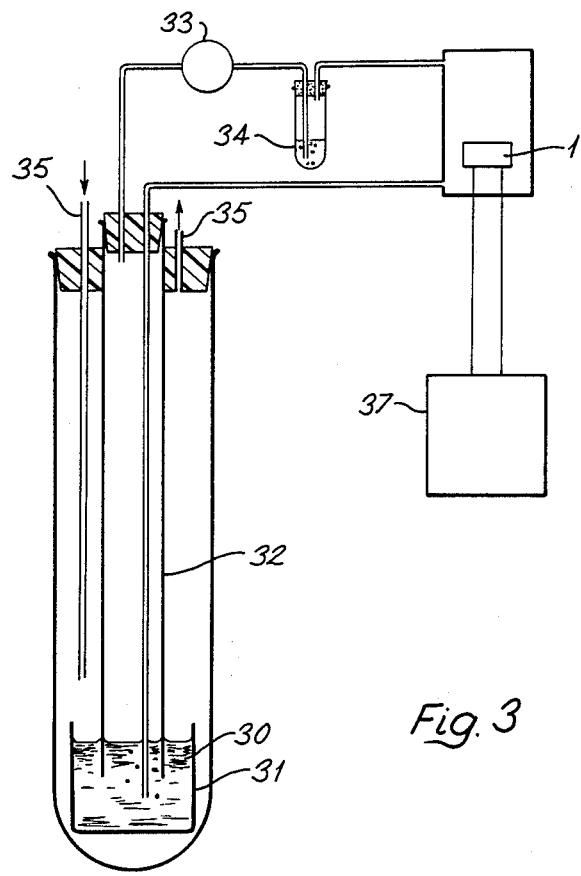
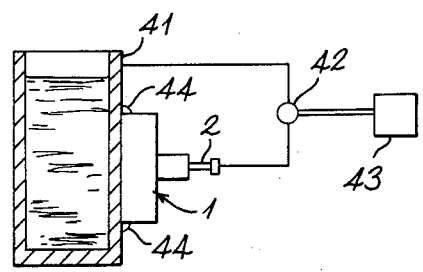
Fig. 3
Fig. 4

ELECTROCHEMICAL SENSOR FOR HYDROGEN SENSING

This invention relates to an electrochemical sensor for hydrogen. (For this purpose, all isotopes of hydrogen are included.) Because hydrogen embrittles structural metals, especially steels, the detection and measurement of dissolved hydrogen in solid or even molten metal are important endeavours. The detection of some parts per million of hydrogen in a gas (e.g. air) or in a liquid (e.g. water) can also be required on occasion.

UK Patent GB 2128751B describes an electrochemical sensor for hydrogen where the hydrogen was detected by its effect on the potential between the electrodes of the cell $Pt,H_2 | HUP | H_xWO_3$ (HUP is hydrogen uranyl phosphate, a solid-state proton conductor.) The $H_xWO_3$ tungsten bronze acted as a reversible hydrogen acceptor and reference, the $WO_3$ lattice itself remaining unchanged.

We have found that a reliable reference may be provided by a metal having a choice of oxidation states, the metal redox reaction comprising the reference.

According to the present invention, an electrochemical sensor for hydrogen comprises (i) an electronically conductive component exposable to the hydrogen to be sensed and which catalyses the dissociation of hydrogen to hydrogen ions, (ii) a solid-state electrolyte for hydrogen cations in contact with the component (i), and (iii) a reference entity in contact with the electrolyte (ii) and connectable to one side of a voltmeter whose other side is connectable to the component (i), characterised in that the reference entity (iii) is a redox mixture, preferably a solid mixture of two oxidation states of the same element. The redox mixture could be Pb(II)/Pb(IV), but a mixture having an $E^o$ of magnitude not exceeding 1 volt versus the standard hydrogen electrode is preferred. Salts are preferred to oxides, and hydrated materials are preferred to anhydrous materials.

Thus the reference entity may comprise for example Fe(II)/Fe(III), such as in the form of the hydrated sulphates, Pd(0)/Pd(II), such as in the form of a hydride, Sn(II)/Sn(IV), Ce(III)/Ce(IV), or Cu(I)/Cu(II). The first is preferred, for its long-term stability. Preferably the reference entity further comprises (preferably in intimate admixture) a hydrogen-ion conductor, preferably the same material as the electrolyte (ii).

The electrolyte (ii) may be a perfluorinated sulphonic acid such as "Nafion" (trade mark).

The conductive component (i) may be a noble metal which catalyses the dissociation of hydrogen to hydrogen ions, such as platinum e.g. as platinum black, preferably applied to the perfluorinated sulphonic acid electrolyte as a slurry in a solution of the same acid and allowed to dry (to give an inseparable coating).

The electrolyte (ii) may be a sheet material, with the component (i) and the reference entity (iii) either sandwiching it or being spaced widely apart on it. To protect it from interfering gases, the component (i) may be covered by a hydrogen-permeable membrane, which may itself constitute the electrolyte (ii).

The invention also provides a method of measuring the concentration or sensing the presence of hydrogen, comprising exposing the conductive component of a sensor as set forth above to the hydrogen (whether in a solid (e.g. a metal), liquid or gas (e.g. air or a non-oxidising gas such as argon or nitrogen)) to be measured, and measuring the voltage generated between the conductive component and the reference electrode.

A by-product of metallic corrosion is commonly the production of hydrogen gas. Therefore, as one application, the invention provides a method of detecting or measuring corrosion of a metal, comprising measuring the concentration of hydrogen in it by the method set forth above. Excessively strong cathodic protection of a metal component can also cause hydrogen to be produced on the metal. In another application, therefore, the invention provides a method of detecting excessive cathodic protection of a metal, comprising measuring the concentration of hydrogen in it by the method set forth above. During electroplating, hydrogen may be so deposited with the metal, and in another application the invention provides a method of detecting hydrogen which has been co-deposited during electroplating, comprising measuring the concentration of hydrogen in the electroplated product by the method set forth above.

Figure 1A:
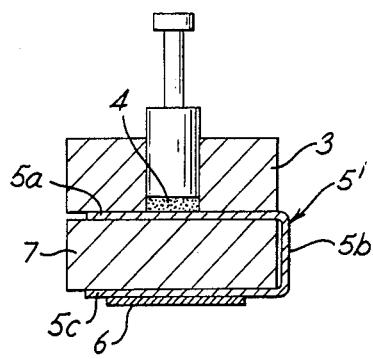
Figure 1B:
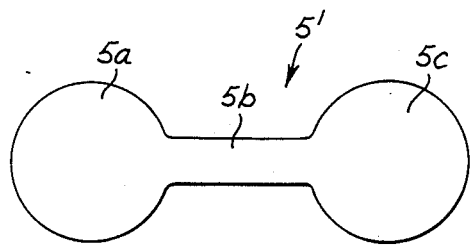
Figure 2:
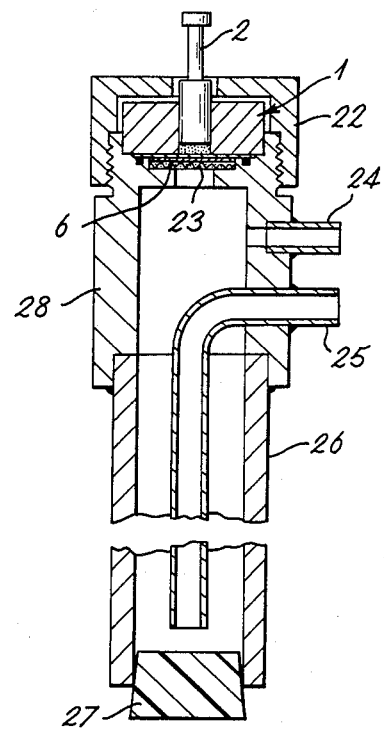

The invention will now be described by way of example with reference to the accompanying drawings, in which FIG. 1 is a schematic cross section of a sensor according to the invention, FIG. 1a shows a modification of the FIG. 1 sensor, FIG. 1b shows a component of the FIG. 1a sensor, FIG. 2 shows apparatus used for calibrating the sensor of FIG. 1, FIG. 3 shows the sensor in use detecting hydrogen in molten metal, and FIG. 4 shows the sensor in use detecting hydrogen in (solid) steel.

Turning to FIG. 1, a sensor according to the invention will be described by reference to how it was made.

A 22 mm diameter disc 5 was cut from a sheet of Nafion 117 (trade mark) and soaked in water. (Nafion is a perfluorinated sulphonic acid which can conduct protons.) Some water was absorbed causing the disc to swell slightly. The disc after being dried in air was cemented by impact adhesive to close the end of a thick-walled tube 3 of Tufnol (trade mark), a rigid inert insulating material.

A slurry of platinum black in commercially available alcoholic Nafion solution was prepared by adding the solution to the platinum black under an argon atmosphere in an ultrasonic mixer. The argon atmosphere was to stop the platinum black from catalysing oxidation of the alcohol solvent. The slurry was applied with a brush to the external face of the disc 5 to form (after drying and heating to 100° C.) a hydrogen-exposable electrode 6.

As an alternative (not illustrated) to the procedure in the foregoing paragraph, a hydrogen-exposable electrode can be applied as follows. Foil, 0.05 mm thick, of 23% silver palladium, through which elemental hydrogen can diffuse, is fixed over the surface of the Nafion disc 5 with impact adhesive around the edge. Even in this case, the Nafion disc is preferably pretreated with the described slurry so as to incorporate platinum black.

From 0.1 g to 0.2 g of a reference mixture 4 of ground powder was placed inside the tube 3 and a stainless steel ram 2 fitted under gentle pressure; the ram acts also as a terminal. The reference mixture 4 and the hydrogen-exposable electrode 6 thus sandwich the proton-conducting disc 5.

The reference mixture 4 was equal masses of FeSO$_4$ and Fe$_2$(SO$_4$)$_3$ hydrates, with a sprinkling of Nafion powder, all well mixed.

FIG. 1a shows a modification of this sensor. The ram 2, thick-walled tube 3 and reference mixture 4 are as described in FIG. 1. A Nafion sheet 5', soaked in water and dried in air, was cut to the shape shown in FIG. 1b, and part 5a of the sheet was cemented to close the end of the tube 3, retaining the reference mixture 4.

Clamping that part 5a of the sheet 5', and/or cemented to it, is a solid Tufnol block 7, down the side of which was cemented part 5b and across the bottom face of which was cemented part 5c of the Nafion sheet 5'. Platinum black was applied as previously described (using slurry) to the bottom face of 5c (remote from 5a) to form a hydrogen-exposable electrode 6 in continuous ionic communication via 5c-5b-5a with reference mixture 4.

This modification minimises any problems which might arise if hydrogen were to diffuse through the Nafion disc 5 of FIG. 1 into the reference mixture 4. That property could however even be exploited, as follows.

There is a need to be able to measure hydrogen in chlor-alkali cells. The problem in using the sensor of FIG. 1 or FIG. 1a is that the platinum black at 6 will catalyse the reaction between the hydrogen and chlorine. In the presence of chlorine or even oxygen, the sensor of FIG. 1 can therefore give non-proportional results, as the dissociation of hydrogen to ions (which the sensor detects) has to complete with the reduction of chlorine or oxygen by the hydrogen (which the sensor cannot detect). If a hydrogen-permeable metallic membrane is used to shield the platinum, the chlorine will attach the membrane. However, if considered sufficiently hydrogen-permeable, the Nafion sheet 5a may itself be used as such a membrane in the FIG. 1a sensor with the platinum black of 6 being placed on its reverse side, i.e. between 5a and 7. Alternatively, a thinner hydrogen-permeable chlorine-impermeable membrane may be used to protect the sensor of FIG. 1 or FIG. 1a such a a proprietary stretch-wrap film. In this way, true readings of hydrogen concentration an be obtained in the presence of interfering gases.

The calibration of the sensor of FIG. 1 was performed as described with reference to FIG. 2. The sensor (1) was mounted between a screw-top backing ring 22 and a cylinder 28 with its hydrogen-exposable electrode (6) contacted by a stainless steel gauze 23. An inlet gas line 24, an outlet gas line 25 (both equipped with water bubblers, not shown), a stainless steel tube 26 and a bung 27 are arranged as shown, and the line 24 was used to contact the electrode 6 with various hydrogen/argon and deuterium/argon mixtures of known composition. Experiments at elevated temperature were conducted by immersion of the apparatus in a water bath with the terminal 2 clear of the water. The sensor voltage was measured by a high impedance ($10^{14}\Omega$) electrometer. Long-term voltage stability of a cell was monitored with pure hydrogen. Response of the illustrated and alternative cells appeared to be identical except that the latter cell, while slower to equilibrate at 'ppm' concentrations of hydrogen, showed no long-term drift in dry hydrogen even with Pb(II)/Pb(IV) reference.

FIG. 3 shows apparatus for detecting hydrogen in molten metal. The metal 30 in an alumina crucible 31 under an atmosphere of argon (in at 35, out at 36) was kept molten by means of an induction coil. A quartz shroud 32 was positioned to dip into the molten metal (in fact aluminium), shielding a space from the argon. A recirculating pump 33 caused gas to flow in a closed circuit including a water bubbler 34, the hydrogen sensor 1, the molten metal and the shroud 32. The voltage output of the sensor 1 is measured and recorded by a voltmeter/chart recorder 37. This equilibration with gas could of course be carried out with any other molten metal, e.g. steel.

FIG. 4 shows apparatus for detecting hydrogen in (solid) steel which, for demonstration purposes, is electrochemically charged with hydrogen. The hydrogen sensor 1 was clamped to the flat surface of a steel vessel 41. A smear of silicone-based vacuum grease 44 was applied to exclude air and to serve as a medium for the transfer of hydrogen atoms to the sensor electrode. The steel was charged with hydrogen by filling the steel vessel 41 with 17 wt % of hydrochloric acid solution. A voltmeter 42 was connected between the vessel 41 and the ram 2 of the sensor 1, and its output charted by a recorder 43.

We claim:

1. An electrochemical sensor for hydrogen, comprising
    (i) an electronically conductive component exposable to the hydrogen to be sensed and which catalyses the disassociation of hydrogen to hydrogen ions,
    (ii) a solid-state electrolyte for hydrogen cations in contact with the component (i), and
    (iii) a reference entity in contact with the electrolyte (ii) and connectable to one side of a voltmeter whose other side is connectable to the component (i),
    said reference entity (iii) comprising a solid mixture of two oxidation states of the same element.
2. A sensor according to claim 1, wherein the mixture comprises salts.
3. A sensor according to claim 1, wherein the mixture is Pb(II)/Pb(IV).
4. A sensor according to claim 1, wherein the mixture has an E$^o$ of magnitude not exceeding 1 volt versus the standard hydrogen electrode.
5. A sensor according to claim 4, wherein the mixture is Sn(II)/Sn(IV), Ce(III)/Ce(IV) or Cu(I)/Cu(II).
6. A sensor according to claim 4, wherein the mixture is Fe(III)/Fe(III).
7. A sensor according to claim 6, wherein the iron is present as hydrated sulphates.
8. A sensor according to claim 4, wherein the mixture is Pd(O)/Pd(II).
9. A sensor according to claim 8, wherein the palladium is present as metal and hydride.
10. A sensor according to claim 1, wherein the redox mixture is intimately admixed with a hydrogen-ion conductor.
11. A sensor according to claim 10, wherein the admixed hydrogen-ion conductor is the same material as the solid-state electrolyte (ii).
12. A sensor according to claim 1, wherein the electronically conductive component (i) is a noble metal.
13. A method of sensing the presence or measuring the concentration of hydrogen, comprising:
    providing an electrochemical sensor for hydrogen comprising (i) an electronically conductive component exposable to the hydrogen to be sensed and which catalyses the disassociation of hydrogen to hydrogen ions, (ii) a solid-state electrolyte for hydrogen cations in contact with the component (i), and (iii) a reference entity in contact with the electrolyte (ii) and connectable to one side of a voltmeter whose other side is connectable to the component (i), the reference entity (iii) comprising a solid mixture of two oxidation states of the same element;

exposing the electronically conductive component (i) of said sensor to the hydrogen to be sensed; and measuring the voltage generated between the electronically conductive component (i) and the reference entity (iii).

* * * * *

UNITED STATES PATENT AND TRADEMARK OFFICE
CERTIFICATE OF CORRECTION

PATENT NO.  :  4,879,005

DATED       :  November 7, 1989

INVENTOR(S) :  FRAY et al

It is certified that error appears in the above-identified patent and that said Letters Patent is hereby corrected as shown below:

Column 4 line 50, delete "Fe(III)/Fe(III)" and replace by
   --Fe(II)/Fe(III)--

Signed and Sealed this

First Day of October, 1991

Attest:

HARRY F. MANBECK, JR.

Attesting Officer

Commissioner of Patents and Trademarks